(12) United States Patent
Larsen

(10) Patent No.: US 10,966,735 B1
(45) Date of Patent: Apr. 6, 2021

(54) SURGICAL DEVICE AND METHOD FOR PERFORMING ARTHRODESIS

(71) Applicant: Eric M. Larsen, Pace, FL (US)

(72) Inventor: Eric M. Larsen, Pace, FL (US)

( * ) Notice: Subject to any disclaimer, the term of this patent is extended or adjusted under 35 U.S.C. 154(b) by 140 days.

(21) Appl. No.: 16/417,058

(22) Filed: May 20, 2019

Related U.S. Application Data

(60) Provisional application No. 62/751,569, filed on Oct. 27, 2018.

(51) Int. Cl.
*A61B 17/17* (2006.01)
*A61B 17/15* (2006.01)
*A61B 17/88* (2006.01)
*A61B 17/80* (2006.01)

(52) U.S. Cl.
CPC .......... *A61B 17/1728* (2013.01); *A61B 17/15* (2013.01); *A61B 17/80* (2013.01); *A61B 17/8897* (2013.01); *A61B 17/1775* (2016.11); *A61B 17/1782* (2016.11)

(58) Field of Classification Search
CPC .................. A61B 17/1728; A61B 17/1717
See application file for complete search history.

(56) References Cited

U.S. PATENT DOCUMENTS

| | | | | |
|---|---|---|---|---|
| 4,776,330 A * | 10/1988 | Chapman | ............. | A61B 17/725 606/64 |
| 5,041,116 A * | 8/1991 | Wilson | ................. | A61B 17/746 606/65 |
| 5,667,510 A * | 9/1997 | Combs | ............... | A61B 17/8004 606/86 R |
| 5,688,279 A * | 11/1997 | McNulty | ............. | A61B 17/155 606/88 |
| 7,011,665 B2 * | 3/2006 | Null | .................... | A61B 17/1728 606/99 |
| 8,231,627 B2 * | 7/2012 | Huebner | ............ | A61B 17/8023 606/86 B |
| 9,622,805 B2 * | 4/2017 | Santrock | ............ | A61B 17/1682 |
| 9,936,995 B2 * | 4/2018 | Dacosta | ................. | A61B 17/17 |
| 2003/0105461 A1 * | 6/2003 | Putnam | .............. | A61B 17/8033 606/311 |
| 2005/0027301 A1 * | 2/2005 | Stihl | .................. | A61B 17/1728 606/96 |
| 2007/0073306 A1 * | 3/2007 | Lakin | ................... | A61B 17/155 606/87 |
| 2008/0140130 A1 * | 6/2008 | Chan | .................. | A61B 17/8605 606/280 |

(Continued)

*Primary Examiner* — Christian A Sevilla
(74) *Attorney, Agent, or Firm* — Suzanne Kikel

(57) ABSTRACT

A surgical device and method for performing arthrodesis are disclosed. The device includes a bone fixation plate, a jig, and a guiding unit. The plate has several fastener-accommodating apertures. The jig has a base for engaging the plate with several bolt-accommodating apertures positioned to align with the plate apertures and a cannulated guide attached to the jig's arm. The cannulated guide has a bore. The arm is oriented at an oblique angle relative to the jig's base. The guiding unit has a first end with a wire guide tube and a drill guide tube affixed to its second end. The wire guide tube and the drill guide tube have an outer diameter with a diameter less than the inner diameter of the cannulated guide of the jig so as to enter into the cannulated guide for the fusion process.

18 Claims, 4 Drawing Sheets

(56) References Cited

U.S. PATENT DOCUMENTS

| | | | |
|---|---|---|---|
| 2009/0143825 A1* | 6/2009 | Graham | A61B 17/1739 606/286 |
| 2011/0054474 A1* | 3/2011 | Metzinger | A61B 17/72 606/64 |
| 2011/0264149 A1* | 10/2011 | Pappalardo | A61B 17/8019 606/286 |
| 2012/0010719 A1* | 1/2012 | Reiley | A61F 2/4606 623/21.18 |
| 2012/0071934 A1* | 3/2012 | Brandon | A61B 17/8047 606/286 |
| 2012/0089192 A1* | 4/2012 | Biedermann | A61B 17/1728 606/280 |
| 2014/0249581 A1* | 9/2014 | Stachniak | A61B 17/7041 606/264 |
| 2016/0317161 A1* | 11/2016 | Garcia | A61B 17/808 |
| 2017/0027702 A1* | 2/2017 | Goldstein | A61B 17/1666 |
| 2017/0340358 A1* | 11/2017 | Bullard | A61B 17/1757 |

* cited by examiner

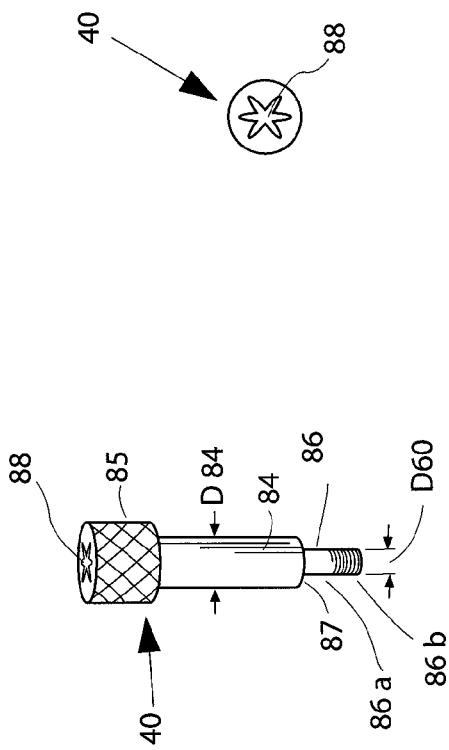
FIG. 4A
FIG. 4
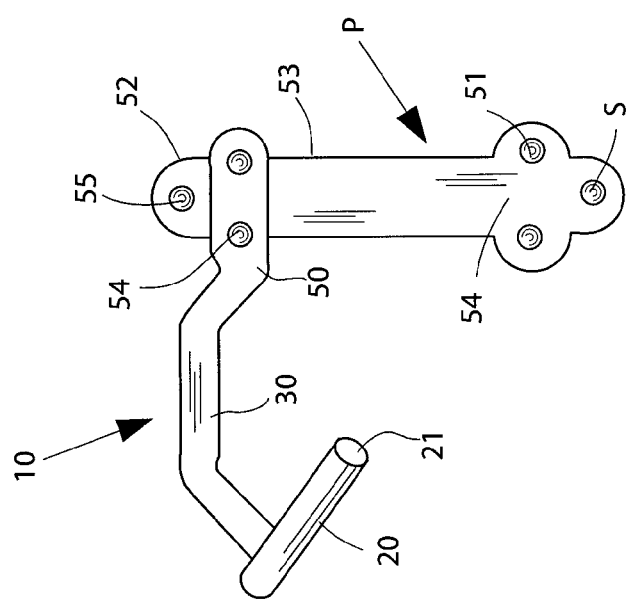
FIG. 3

SURGICAL DEVICE AND METHOD FOR PERFORMING ARTHRODESIS

CROSS REFERENCE TO RELATED APPLICATIONS

This application claims priority to U.S. provisional patent application Ser. No. 62/751,569 filed Oct. 27, 2018, entitled Perfect Lag Screw Technology, the disclosure of which is incorporated herein by reference in its entirety.

BACKGROUND OF THE INVENTION

1. Field of the Invention

The present invention relates to the general field of surgery, and more particularly to arthrodesis, commonly known as bone fusion surgery.

2. Brief Description of the Prior Art

The human skeleton is composed of 206 individual bones that perform a variety of important functions, such as, support, movement, protection, storage of minerals, and formation of blood cells. These bones can be grouped into two categories: the axial skeleton and the appendicular skeleton. The axial skeleton consists of 80 bones that make the body's center of gravity, and the appendicular skeleton consists of 126 bones that make up the body's appendages. The axial skeleton includes the skull, the vertebral column, the ribs, and the sternum, among other body parts, and the appendicular skeleton includes the long bones of the upper and lower limbs, the clavicles, and other bones that attach these long bones to the axial skeleton, among other body parts.

Over time, arthritis can cause severe damage to the body joints. If some medical treatments have not successfully alleviated the pain associated with arthritis, joint fusion surgery may be required. Arthrodesis is a procedure which fuses or "welds" together two segmented bones which make up an arthritic joint or a fractured joint, and which procedure causes the segmented bones to become one solid bone. That is, arthrodesis is defined as a surgical immobilization of a joint by fusion of the adjacent bones. This procedure may lessen the pain associated with arthritis and/or a fracture, and in general, will make the joint more stable. Joint fusion surgery can be done on many different joints; such as, for example, on a patient's spine, ankles, wrists, fingers, thumbs, toes, and feet. Also, joint fusion surgery may also be used for fixating a damaged bone joint or a fracture.

Several methods and apparatuses are known in the art for fixating a damaged bone joint or a fracture in order to allow bone fusion to occur. Some conventional bone fixation systems include a bone fixation plate having apertures for receiving fixation members, such as screws, which are configured to attach to an underlying bone that includes, at a minimum, two bone segments separated by a bone gap. The bone gap may be a fracture created by a traumatic event or an osteotomy, or the bone gap may be the result of the debridement of a joint of two discrete bones joined together in an arthodesis procedure. Thus, the bone fixation plate may be affixed to the bone on opposite sides of the bone gap via the screws which are fixated in each bone segment in order to promote the union of the bone segments in the healing of the fracture or ossification of the joint.

Bone fixation systems may also involve Kirschner wires (K-wires) which are temporarily inserted into the apertures in the bone fixation plate and into the underlying bone segments in order to determine the proper length, the rotation, and the alignment of the bone segments prior to attaching the permanent bone fixation plate onto the underlying bone segments. Once the bone fixation plate has been properly positioned, the permanent bone screws are generally inserted into one or more of the apertures of the bone fixation plate to attach the bone fixation plate permanently to the underlying bone segments. Generally, the apertures of the bone fixation plate for receiving the permanent screws are located on opposite sides of bone fixation plate and therefore on opposite sides of the bone gap such that the permanent screws are received in the separated bone segments for affixing the bone fixation plate to the underlying bone for joining the bone segments together.

In a conventional bone fixation system, a K-wire may be screwed or otherwise driven through the same apertures for receiving the screws of the bone fixation plate on opposite sides of the bone gap. The K-wire is generally smaller in diameter compared to the diameter of the screw apertures, and the K-wire is positioned so as to bear against the opposing edges of the respective screw apertures in order to prevent movement of the bone fixation plate during imaging, such as fluoroscopy.

A bone fixation plate and fasteners, such as screws, are widely used in a variety of orthopedic applications. The bone fixation plate and screws are generally used to align, mend, and/or alter adjacent bone segments of a patient. The correct orientation and alignment of these fasteners or screws are generally important for proper engagement and positioning of the bone fixation plate relative to the bone segments. In a typical procedure, the opposing bone surfaces of a joint or fracture are first made planar by sawing and/or smoothing. Next, a bore is drilled through the joint or fracture, and a compression screw is then inserted into the bore and a compressive force is applied to the joint or fracture to cause the fusion process to occur.

In the instance of small bones and joints of the fingers and/or toes, the integrity of a fused joint is often dependent upon the skill of the surgeon in accurately positioning and aligning the cutting and drilling instruments to make properly angled cuts and bores. Although it is well known in the art for a surgeon to use a temporary bone fixation plate or guide to achieve precise angles in certain cutting and drilling procedures, the techniques and instruments commonly in use today are generally ill-suited for fusion procedures on small bones, such as those in the fingers and/or toes.

As stated herein above, it is common practice in the field of arthrodesis to use a bone fixation plate and a corresponding compression screw to stabilize and compress the joint or fracture together in order to allow the joint or fracture to fuse. In one configuration, the bone fixation plate is affixed directly to the bone which is to be repaired and the compression screw is then inserted into one of the apertures in the bone fixation plate and then into the bore drilled through the damaged joint or fracture. The compression screw is anchored in the distal end of the joint/fracture and engages the bone fixation plate to create a compressive force. Examples of bone fixation plates and compression screws are disclosed in U.S. Pat. No. 4,776,330 to Chapman et al. and U.S. Pat. No. 5,041,116 to Wilson.

Arthrodesis is generally defined as a surgical immobilization of a joint by fusion of the adjacent bones. In the field of arthrodesis, a best practice is to use a lag screw which is a screw that is positioned across a joint for pulling the adjacent bones together in order to fuse the joint. Oftentimes, the insertion of this lag screw may be intercepted or blocked for travel across the joint by the screws in the bone fixation plate. That is, the lag screw when inserted may run into the screws already inserted in the bone fixation plate and these latter screws may prevent the lag screw from being positioned across the bone segments which are to be fused together.

There is, therefore, a need in the art for a joint fixation system that allows a surgeon to accurately and efficiently perform arthrodesis or fusion on the joints, such as fingers.

There is a further need in the art to provide a surgical device and method of use of the surgical device which overcomes the drawbacks of the prior art and which may be used on joints such as those in fingers, toes, ankles, feet, hands, and legs.

SUMMARY OF THE INVENTION

The present invention provides such needs. The present invention provides a surgical device and method for performing arthrodesis. The surgical device comprises a jig that attaches to a metal bone fixation plate used in bone surgeries, such as fusing adjacent bones together. Currently, the practice is to eye ball the placement of the lag screw during joint fusion. This practice invariably raises the possibility that the lag screw generally used in joint fusion will run into or be blocked by the screws associated with the bone fixation plate. The surgical device of the present invention is used to prevent the lag screw used in joint fusion from running into the screws associated with the bone fixation plate.

In an embodiment of the present invention, the jig of the surgical device is temporarily attached to a locking bone fixation plate that is used for fixation during arthrodesis. The surgical device of the present invention uses existing lock apertures and has two or more points of fixation in order to ensure a secure and consistent angulation of the surgical device. The surgical device utilizes different sized cannulas to allow for guide wire, drill and screw fixation without removing the jig. As stated herein above, a cannula is a small tube for insertion into a body cavity or into a duct or vessel. A cannulated guide of the jig of the invention is double ended. One end is a guide for the wire, and the other end is a guide for the drill.

In an embodiment of the present invention, the surgical device for use in arthrodesis comprises a bone fixation plate, a jig and a guiding unit. The bone fixation plate has a first end, a second end, a central section connecting the first end to the second end; a plurality of first fastener-accommodating apertures adjacent to the first end; and a second plurality of fastener-accommodating apertures adjacent to the second end of the bone fixation plate. This bone fixation plate may have an arcuate configuration for abutting against the contour of a joint of a finger and/or a toe. The jig has a base adapted to abut the bone fixation plate. The base of the jig has a plurality of fixation bolt-accommodating apertures defined therethrough. Each of the fixation bolt-accommodating apertures in the base of the jig has a diameter and is located such as to be in alignment with an associated fastener-accommodating aperture of the bone fixation plate when the base is operably associated with the bone fixation plate. In a further embodiment of the invention, the surgical device may be comprised of a jig and a guiding unit which are used with a bone fixation plate already available in the market place.

The jig further comprises: a first arm having one end integral with the base of the bone fixation plate and a second end spaced away from the first end of the jig; and a cannulated guide fixed to the second end of the arm of the jig to be oriented at an oblique angle relative to the base of the jig. The guiding unit has a body with a first end and a second end; a wire guide tube fixed to the first end of the body of the guiding unit, the wire guide tube having a wire insertion aperture defined therein; and a drill guide tube fixed to the second end of the body of the guiding unit, the wire guide tube and the drill guide tube each having an outer diameter with a dimension less than that of the inner diameter of the cannulated guide of the jig.

The temporary fixation bolt has a body with an outer diameter greater than the diameter of the temporary fastener bolt accommodating apertures defined through the base of the jig to abut the base of the jig adjacent to a bolt-accommodating aperture associated therewith and to prevent the body of the temporary fixation bolt from passing into its associated fixation bolt-accommodating aperture. The temporary fixation bolt has a knurled head and a slot defined in its head, the slot being configured to receive a screw driver. The bone fixation plate and the jig have corresponding arcuate configurations.

A method of the invention for performing an arthrodesis procedure with the surgical device of claim 1, comprises the steps of: (a) attaching the jig to the bone fixation plate with a temporary fixation bolt; (b) preparing a patient's joint for fusion; (c) temporarily fixating the bone fixation plate P to a patient's bone; (d) attaching a proximal portion of the bone fixation plate P to the patient's bone; (e) inserting a wire guide tube into the cannulated guide of the jig; (f) driving a guide wire through the wire guide tube and across and over a patient's joint to be fused; (g) removing the wire guide tube from the cannulated guide of the jig and rotating the guiding unit so as to align the drill guide tube with the cannulated guide of the jig, and inserting the drill guide tube into the cannulated guide of the jig; (h) drilling over the guide wire; (i) removing the drill guide tube from the cannulated guide of the jig; (j) sliding a cannulated or solid screw through the cannulated guide of the jig, onto the guide wire and across the patient's joint; (k) removing the guide wire and the jig; and (l) filling the remaining accommodating apertures in bone fixation plate with screws.

These and other features, methods, and advantages of the present invention will be better appreciated and understood when the following description is read in light of the accompanying drawings.

BRIEF DESCRIPTION OF THE DRAWINGS

The components in the figures are not necessarily to scale, emphasis instead being placed upon illustrating the principles of the invention. Moreover, in the figures, like referenced numerals designate corresponding parts throughout the different views.

FIG. 3 is an elevational view of the jig of FIG. 1 attached to a bone fixation plate of the invention.

FIG. 4 is an elevational view of a temporary fixation bolt used in conjunction with the jig and bone fixation plate of the present invention.

FIG. 4A is a top plan view of the temporary fixation bolt of FIG. 4.

DETAILED DESCRIPTION OF THE INVENTION

Figure 6:
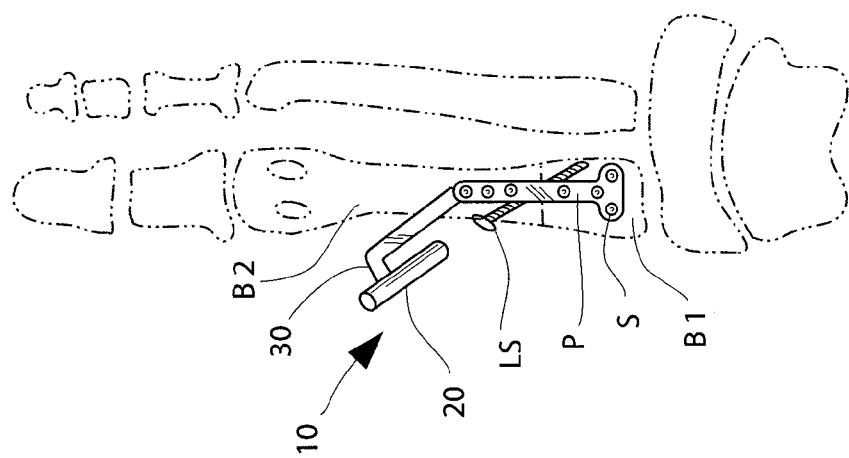
FIG. 6 is a top schematic view of the surgical device of the invention being used on a first metatarsal cuneiform joint fusion process.
Figure 5:
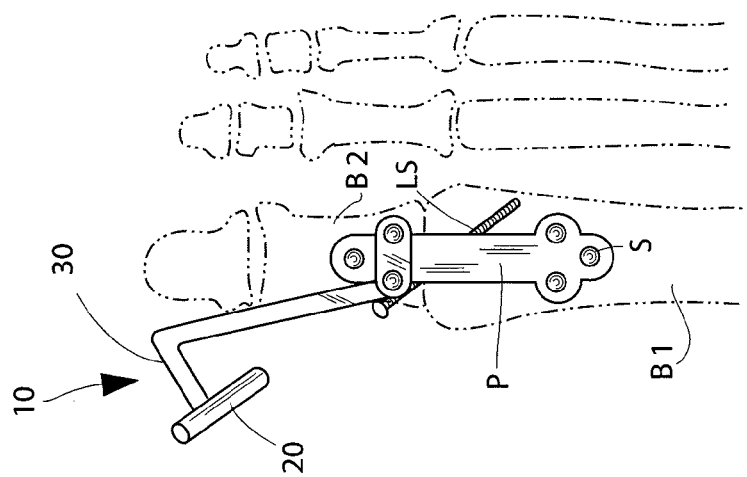
FIG. 5 is a top schematic view of the surgical device of the invention being used on a first metatarsal phalangeal joint fusion process.
Figure 7:
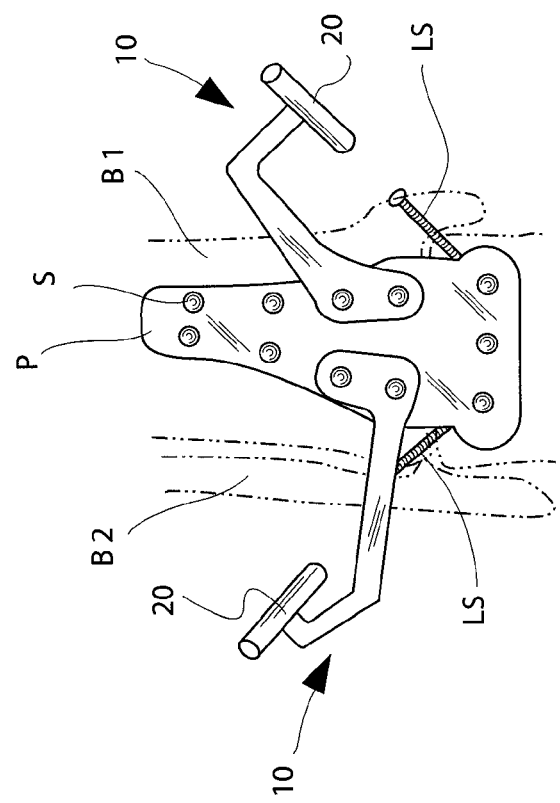
FIG. 7 is a top schematic view of the surgical device of the invention being used in an ankle fusion process.

Referring to FIGS. 1 through 8, the present invention is a surgical device for use in arthrodesis by a surgeon for fusing bones together, such as indicated by references B1 and B2 in FIGS. 5, 6 and 7.

Figure 1:
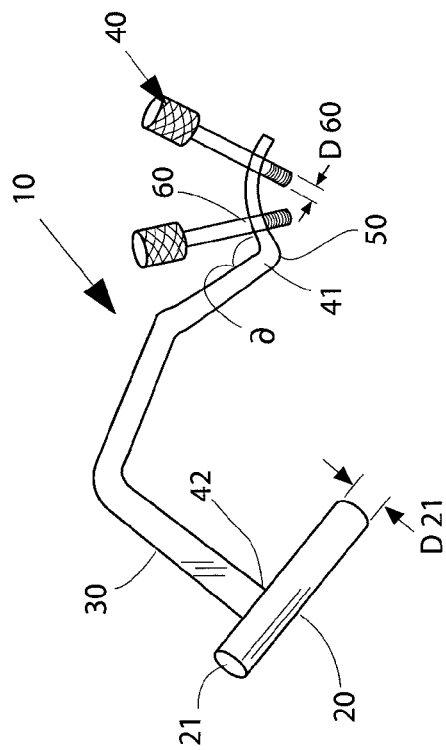
FIG. 1 is an elevational view of a jig of the surgical device of the present invention.

As best shown in FIG. 1, the surgical device of the invention comprises a jig 10 and a bone fixation plate P as shown in FIG. 3. With reference to FIG. 1, jig 10 is comprised of a cannulated guide 20 which is a hollow tube having a bore 21 with an internal diameter $D_{21}$. In general, a cannula is a small tube for insertion into a body cavity or into a duct or vessel. Cannulated guide 20 is attached to an arm 30 which is integral with a base 50 and is oriented at a precise oblique angle α with respect to base 50. Arm 30 has a first end 41 which is integral with base 50 and a second end 42 which is attached to cannulated guide 20 and which second end 42 is spaced away from first end 41 of jig 10. As shown in FIGS. 1 and 3, arm 30 terminates with a contoured base 50, and which as shown in FIG. 3, is located above bone fixation plate P which will be implanted into the patient and attached to the bone segments of a patent by screws S, one of which is indicated in FIG. 3. Cannulated guide 20 and bone fixation plate P are comprised of a rigid material, such as, for example, metal and plastic. In an embodiment of the invention, cannulated guide 20 and bone fixation plate P are made of metal.

Even though not precisely shown in FIG. 3, it is to be appreciated that bone fixation plate P is generally in an arcuate configuration. Bone fixation plate P has a first end 51, a second end 52, and a central section 53 connecting first end 51 and second end 52 together. The curvature of bone fixation plate P is selected so that it fits snugly and properly against the bones of the patient, as can be understood from FIG. 5. As particularly shown in FIG. 3, first end 51 of bone fixation plate P has a plurality of first fastener-accommodating apertures, one of which is indicated by reference numeral 54, and the second end 52 of bone fixation plate P has a plurality of second fastener-accommodating apertures, one of which is indicated by reference numeral 55.

Referring again to FIG. 1, base 50 of jig 10 includes a plurality of fixation bolt-accommodating apertures such as that indicated by reference numeral 60. Each of fixation bolt-accommodating apertures 60 in base 50 of jig 10 has a diameter D60 and is positioned to be aligned with an associated first fastener-accommodating aperture 54 and/or with second fastener-accommodating aperture 55 of bone fixation plate P when base 50 is operably positioned relative to bone fixation plate P, as best illustrated in FIG. 3.

Still referring to FIG. 1, two temporary fixation bolts 40 are tap-in bolts and are used to firmly secure jig 10 to bone fixation plate P in preparation for arthrodesis. Bolts 40 are received in apertures 54, which are aligned with apertures in bone fixation plate P in order to affix jig 10 to bone fixation plate P. One such temporary fixation bolt 40 is best illustrated in FIG. 4. As shown therein, temporary fixation bolt 40 has a smooth body 84 and a knurled head 85 on one end, and a tip 86 on the other end. Tip 86 has an externally threaded portion 86b and a smooth portion 86a. Tip 86 also has an outer diameter D60 which is less in dimension than the outer diameter D84 of body 84 of fixation bolt 40 such that a ledge 87 is defined at the intersection of smooth body 84 and tip 86. Ledge 87 abuts bone fixation plate P in order to ensure proper positioning of jig 10 with respect to bone fixation plate P. The externally threaded portion 86b of tip 86 fits through jig 10 as shown in FIG. 1 and extends through apertures of the bone fixation plate P of FIG. 3. Temporary fixation bolts 40 are essentially tap-in bolts wherein the threaded portion 86b of tip 86 is slightly threaded into a bone of the patient for anchoring jig 10 with bone fixation plate P against the patient's bone for operation of the surgical device of the invention. In this instance, ledge 87 of each bolt 40 abuts against the bone fixation plate in order to prevent the travel of bolts 40 into the patient's bone. As shown in FIG. 4A, the top 88 of temporary fixation bolt 40 has a slot 88 configured to receive a screw driver.

Figure 2:
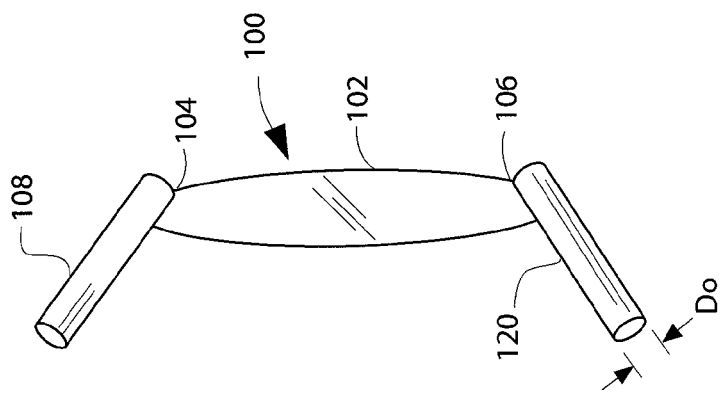
FIG. 2 is an elevational view of a guiding unit of the surgical device of the present invention.

Referring to FIG. 2, the surgical device of the invention further comprises a guiding unit 100. Guiding unit 100 comprises a body 102 having a first end 104 and a second end 106, a wire guide tube 108 and a drill guide tube 120. The wire guide tube 108 is affixed to the first end 104 of body 102 of guiding unit 100. The drill guide tube 120 is affixed to the second end 106 of body 102 of guiding unit 100. Wire guide tube 108 and drill guide tube 120 each have an outer diameter $D_O$ which is less in dimension than inner diameter D21 of cannulated guide 20 of jig 10 of FIG. 1. Guiding unit 100 is comprised of a rigid material, such as, for example, metal and plastic. In an embodiment of the invention, guiding unit 100 is made of metal.

Bone fixation plate P with jig 10 secured thereto is temporarily attached to the bones of a patient with the use of a reduction clamp R or temporary olive wires (not shown), or a combination thereof. In using the surgical device of the present invention, reference is particularly made to FIGS. 1-4 and 8. The cannulated wire guide tube 108 of guiding unit 100 of FIG. 2 is inserted into the cannulated guide 20 of jig 10 of FIG. 1, and a guide wire is passed through wire guide tube 108 and implanted into the bone crossing the joint to be fused. The wire guide tube 108 is pulled back and off of the wire and the cannulated drill guide tube 120 is slid over the wire and into the cannulated guide 20 of jig 10. A drill aperture is then made in the bone crossing the joint to be fused. The drill guide tube 120 is pulled back off of the guide wire and out of the cannulated guide 20. The patient's bone may then be tapped, countersunk, and the depth measured over the wire and through the cannulated guide 20 of jig 10. As best shown in FIGS. 5, 6 and 7, a lag screw LS is then placed onto the guide wire if cannulated, or a solid screw is used, which is inserted through the cannulated guide 20 of jig 10. Bone fixation plate P is then permanently affixed to the patient's bone with screws in a manner well-known to those skilled in the art.

The number of fixation bolts 40 of FIG. 4 needed to affix jig 10 to bone fixation plate P may vary according to the anatomical considerations of the patient. Fixation bolts 40 and the contoured end 50 of jig 10 are perfectly matched to ensure that there is complete contact between the jig and the bone fixation plate P and that the bone fixation plate P will not sit proud on the bone. The portion of bolt 40 that goes through jig 10 is smooth in order to avoid any damage to the threads of the bolt 40. Each bolt 40 has a ledge 87 to hold the jig tightly against the bone fixation plate. Bolt 40 is constructed is to be hand tightened; however, bolt 40 has a slot 88 in its top surface which is configured to allow the use of a screw driver for tightening and loosening the bolt 40 relative to bone fixation plate P.

Figure 8:
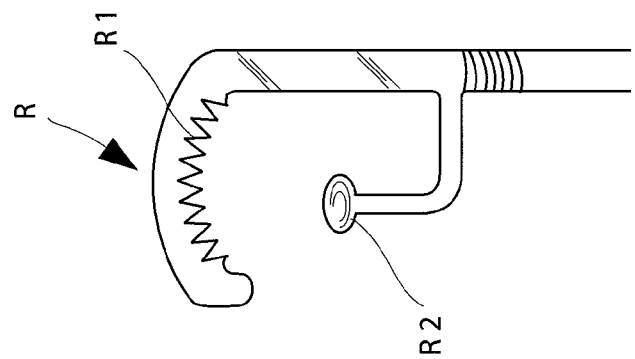
FIG. 8 is an elevational view of a reduction clamp which may be used in conjunction with the surgical device of the invention.

In an embodiment of the invention, jig 10 and bone fixation plate P are temporarily attached to the bones of a patient with the use of a reduction clamp, such as that shown in FIG. 8. Reduction clamp R has a first portion R1 in the shape of a traditional lobster claw reduction clamp and a second portion R2. Second portion R2 generally has a smooth surface and may be spherically shaped. As illustrated in FIG. 8, first portion R1 and second portion R2 of reduction clamp R form a jaw. Second portion R2 is structured to fit into one of the apertures of the surgical device of the invention, without damaging the threads on bone fixation plate P and to affix bone fixation plate P to the patient's bones. With a spherical head on reduction clamp R, the patient's bones will be able to slide between the jaw of reduction clamp R in order to allow compression with lag screw LG without having to remove the reduction clamp R, thereby differing from the use of olive wire for a temporary attachment. Reduction clamp R may be straight, curved or at a 90 degree angle similar to those clamps currently used in arthrodesis or bone fusion surgery. It is to be appreciated that various reduction clamps and reduction clamp tip designs may be used with the surgical device of the invention without departing from the scope of the invention.

The surgical device of the invention consisting of jig 10 and bone fixation plate P is shown in FIG. 5 as being used on the first metatarsal phalangeal joint of a toe, alternative uses of the surgical device of the invention are anticipated. For example, FIG. 6 shows jig 10 and bone fixation plate P in use during a first metatarsal cuneiform joint fusion wherein jig 10 and bone fixation plate P are used on bone segments B1 and B2 of a foot, and FIG. 7 shows two jigs 10 and a bone fixation plate P being used during an ankle fusion wherein B1 is the tibia, B2 is the fibula, and B3 is the talus. From the above teachings, those skilled in the art will appreciate the manner in which the surgical device of the present invention is used in arthrodesis or in bone fusion procedures such as those illustrated in FIGS. 5 through 7. It is to be appreciated that the surgical device of the invention may be adapted for use in other joint fusion procedures for various parts of the body for joining two segmented bones together.

A method of performing arthrodesis with the surgical device of invention comprises the steps of: (a) attaching jig 10 to bone fixation plate P with one or more temporary fixation bolts 40; (b) preparing a patient's joint for fusion surgery; (c) temporarily attaching bone fixation plate P to the patient's bones; (d) attaching a proximal portion of bone fixation plate P to the patient's bone; (e) inserting the wire guide tube 108 of guiding unit 100 into the cannulated guide 20 of jig 10; (f) driving a guide wire through the wire guide tube 108, and across and over a patient's joint to be fused; (g) removing the wire guide tube 108 from the cannulated guide 20 of jig 10, reversing or rotating guiding unit 100 until drill guide tube 120 is in alignment with the cannulated guide 20 of jig 10, and inserting drill guide tube 120 into the cannulated guide 20 of jig 10; (h) drilling over the guide wire; (i) removing the drill guide tube 120 from the cannulated guide 20 of jig 10; (j) sliding a cannulated screw through the cannulated guide 20 of jig 10 toward the guide wire and across the patient's joint; (k) removing the guide wire and jig 10; and (l) filling the remaining bone fixation plate apertures with screws. As stated herein above, the guide wire is a K-wire.

Further steps include performing a countersink in the patient's bone; temporarily attaching the bone fixation plate P of the surgical device of the invention to the patient's bones using a reduction clamp R or alternatively temporarily attaching the bone fixation plate of the surgical device to the patient's bones using an olive wire; placing a lag screw LS onto the guide wire and moving the lag screw LS through the cannulated guide 20 of jig 10; and permanently affixing the bone fixation plate P to the patient's bones.

A further method of performing arthrodesis using the surgical device of the invention comprises the steps of: attaching jig 10 to bone fixation plate P with temporary fixation bolts 40; preparing the joint for fusion; temporarily attaching bone fixation plate P to the patient's bone with reduction clamp R and/or with olive wires; attaching the proximal portion of bone fixation plate P with screws; inserting the wire guide into the cannulated guide 20 of jig 10; driving the guide wire through the wire guide tube 108 and crossed over the joint to be fused; removing the wire guide tube 108 and inserting a drill guide tube into the cannulated guide 20 of jig 10; drilling over the guide wire; removing the drill guide tube 120 of guiding unit 100; if desired, countersinking is performed, and the length of the screw is measured; assuring that the distal portion of bone fixation plate P is not excessively attached in order to allow compression across the joint; sliding a cannulated screw through the cannulated guide 20 of jig 10, onto the guide wire, and across the bone joint; removing the guide wire and jig 10; and filling the remaining apertures in bone fixation plate P with screws.

The surgical device of the present invention may offer the following advantages to surgeons: a) the ability to insert a lag screw during arthrodesis without worrying about interfering with the screws in the bone fixation plate; b) jig 10 can be attached to bone fixation plate P by the surgical technician prior to use, thereby not taking any of the surgeon's time; and c) the lag screw can be thrown percutaneously with confidence. In surgery, a percutaneous procedure is any medical procedure or method where access to inner organs or other tissue is done via a very small opening in the skin, rather than by using an "open" approach where inner organs or tissue are exposed with a larger incision. Often, after drilling over a guide wire, the wire will get stuck in the drill. Once the drill is removed, the exact location and trajectory of the drill hole may be lost. In the invention, with the jig still being in place, the exact location and trajectory of the drill hole are known. A screw may be inserted without excessive damage to the cortical bone which may lead to bone destruction and loss of compression strength from the screw.

The surgical device of the invention may offer the following advantages to the manufacturer: a) it can be used with existing locking bone fixation plates; b) if the manufacturer currently has a bone fixation plate that uses a lag screw in the bone fixation plate, this bone fixation plate may be modified to remove that aperture; c) removing the lag aperture can reduce the thickness of the bone fixation plate which may result in less hardware irritation for the patient, and d) reducing the thickness of the bone fixation plate will decrease costs due to less material, such as metal, generally used in the bone fixation plate.

As stated herein above and as shown in FIGS. 1 and 3, base 50 of jig 10 and bone fixation plate P are in an arcuate configuration. This arcuate configuration may be advantageous in abutting the surgical device of the invention against the contour of the bone segments which are to be fused together, such as a small joint, such as that of a finger or toe. It is to be appreciated, that in some embodiments, base 50 and bone fixation plate P may be flat so that the surgical device of the invention may abut against the contour of larger bone segments.

While the present invention has been described in connection with the preferred embodiments of the various figures, it is to be understood that other similar embodiments may be used or modifications and additions may be made to the described embodiments for performing the same function of the present invention without deviating there from. Accordingly, it is intended by the appended claims to cover all such changes and modifications to come within the spirit and scope of the invention.

What is claimed is:

1. A surgical device for use in arthrodesis, comprising:
a bone fixation plate comprising a first end, a second end, a central section connecting the first end and the second end together, a plurality of first fastener-accommodating apertures defined in the bone fixation plate adjacent to the first end, and a second plurality of fastener-accommodating apertures defined in the bone fixation plate adjacent to the second end of the bone fixation plate;
a jig comprising a first end, a second end, and a base adapted to abut against the bone fixation plate, the base of the jig having a plurality of fixation bolt-accommodating apertures defined therethrough, each of the fixation bolt-accommodating apertures in the base of the jig having a diameter and being located to align with an associated fastener-accommodating aperture defined in the bone fixation plate when the base of the jig is operably associated with the bone fixation plate,
the jig further comprising a first arm with one end integral with the base and a second end spaced away from the first end of the jig; a cannulated guide fixed to the second end of the first arm of the jig oriented at an oblique angle relative to the base of the jig, the cannulated guide having a bore defined therethrough, the bore of the cannulated guide having an inner diameter, and a temporary fixation bolt accommodated in an associated fixation bolt-accommodating aperture defined through the base of the jig; and
a guiding unit comprising a body with a first end and a second end, a wire guide tube affixed to the first end of the body of the guiding unit, and a drill guide tube affixed to the second end of the body of the guiding unit, the wire guide tube and the drill guide tube each having an outer diameter with a dimension less than that of the inner diameter of the bore of the cannulated guide of the jig.

2. The surgical device of claim 1, wherein the temporary fixation bolt associated with the jig has an outer diameter greater than the diameter of the fixation bolt-accommodating apertures defined in the base of the jig for abutting the base of the jig adjacent to a bolt-accommodating aperture associated therewith and to prevent the temporary fixation bolt from passing into the associated fixation bolt-accommodating aperture.

3. The surgical device of claim 2, wherein the temporary fixation bolt has a knurled head.

4. The surgical device of claim 3, wherein the temporary fixation bolt has a slot defined in its head and configured to receive a screw driver.

5. The surgical device of claim 1, wherein the bone fixation plate has an arcuate configuration.

6. The surgical device of claim 5, wherein the base of the jig has an arcuate configuration corresponding to the arcuate configuration of the bone fixation plate.

7. A method of performing arthrodesis with the surgical device of claim 1, the steps comprising:
(a) attaching the jig to the bone fixation plate with at least two temporary fixation bolts;
(b) preparing a patient's joint for fusion;
(c) temporarily fixating the bone fixation plate to a patient's bone;
(d) attaching a proximal portion of the bone fixation plate to the patient's bone;
(e) inserting the wire guide tube into the cannulated guide of the jig;
(f) driving a guide wire through the wire guide tube of the guiding unit, and across and over a patient's joint to be fused;
(g) removing the wire guide tube from the cannulated guide of the jig, rotating the guiding unit, and aligning the drill guide tube with the cannulated guide and inserting the drill guide tube into the cannulated guide of the jig;
(h) drilling over the guide wire;
(i) removing the drill guide tube from the cannulated guide of the jig;
(j) sliding a cannulated screw through the cannulated guide of the jig, onto the guide wire and across the patient's joint;
(k) removing the guide wire and the jig; and
(l) filling the remaining accommodating apertures in bone fixation plate with screws.

8. The method of claim 7, including the step of performing a countersink in the patient's bone.

9. The method of claim 7, further including the step of temporarily attaching the bone fixation plate of the surgical device to the patient's bone using a reduction clamp.

10. The method of claim 7, further including the step of temporarily attaching the bone fixation plate of the surgical device to the patient's bone using a wire.

11. The method of claim 7, further including the step of placing a lag screw onto the guide wire and moving it through the cannulated guide of the jig.

12. The method of claim 11, further including the step of permanently affixing the bone fixation plate to the patient's bone.

13. A surgical device for use in arthrodesis, comprising:
a jig comprising a base adapted to abut against a bone fixation plate, the base of the jig having a plurality of fixation bolt-accommodating apertures defined therethough, each of the fixation bolt-accommodating apertures in the base of the jig having a diameter and being located to align with an associated fastener-accommodating aperture defined in the bone fixation plate when the base of the jig is operably associated with the bone fixation plate,
the jig further comprising a first arm with one end integral with the base of the bone fixation plate and a second end spaced away from the first end of the jig; a cannulated guide fixed to the second end of the arm of the jig oriented at an oblique angle relative to the base of the jig, the cannulated guide having a bore defined therethrough, the bore of the cannulated guide having an inner diameter, and a temporary fixation bolt accommodated in an associated fixation bolt-accommodating aperture defined through the base of the jig; and
a guiding unit comprising a body with a first end and a second end, a wire guide tube affixed to the first end of the body of the guiding unit, and a drill guide tube affixed to the second end of the body of the guiding unit, the wire guide tube and the drill guide tube each having an outer diameter with a dimension less than that of the inner diameter of the bore of the cannulated guide of the jig.

14. The surgical device of claim 13, wherein the temporary fixation bolt associated with the jig has an outer diameter greater than the diameter of the fixation bolt-accommodating apertures defined in the base of the jig for abutting the base of the jig adjacent to a bolt-accommodating aperture associated therewith and to prevent the temporary fixation bolt from passing into the associated fixation bolt-accommodating aperture.

15. The surgical device of claim 14, wherein the temporary fixation bolt has a knurled head.

16. The surgical device of claim 15, wherein the temporary fixation bolt has a slot defined in its head and configured to receive a screw driver.

17. The surgical device of claim 13, wherein the bone fixation plate has an arcuate configuration.

18. The surgical device of claim 17, wherein the base of the jig has an arcuate configuration corresponding to the arcuate configuration of the bone fixation plate.

\* \* \* \* \*